United States Patent [19]
Green

[11] Patent Number: 4,767,044
[45] Date of Patent: * Aug. 30, 1988

[54] SURGICAL FASTENER APPLYING APPARATUS

[75] Inventor: David T. Green, Norwalk, Conn.

[73] Assignee: United States Surgical Corporation, Norwalk, Conn.

[*] Notice: The portion of the term of this patent subsequent to Apr. 8, 2003 has been disclaimed.

[21] Appl. No.: 782,732

[22] Filed: Oct. 4, 1985

Related U.S. Application Data

[63] Continuation-in-part of Ser. No. 662,679, Oct. 19, 1984, Pat. No. 4,580,712.

[51] Int. Cl.⁴ .............................................. A61B 17/00
[52] U.S. Cl. ................................. 227/19; 227/DIG. 1
[58] Field of Search ....... 128/334 R; 227/19, DIG. 1, 227/135

[56] References Cited

U.S. PATENT DOCUMENTS

| | | | |
|---|---|---|---|
| 960,300 | 6/1910 | Fischer . | |
| 2,344,071 | 3/1944 | Wilson et al. | 227/DIG. 1 |
| 3,078,465 | 2/1963 | Bobrov | 227/DIG. 1 |
| 3,079,606 | 3/1963 | Bobrov et al. | 227/DIG. 1 |
| 3,275,211 | 9/1966 | Hirsch et al. | 227/124 |
| 3,317,105 | 5/1967 | Astafjev et al. | 227/76 |
| 3,458,099 | 7/1969 | Schick | 227/111 |
| 3,490,675 | 1/1970 | Green et al. | 227/19 |
| 3,494,533 | 2/1970 | Green et al. | 227/19 |
| 3,499,591 | 3/1970 | Green | 227/76 |
| 3,822,818 | 7/1974 | Strekopytov et al. | 227/124 |
| 4,111,206 | 9/1978 | Vishnevsky et al. | 128/305 |
| 4,241,861 | 12/1980 | Fleischer | 227/135 |
| 4,244,372 | 1/1981 | Kapitanov et al. | 128/334 R |
| 4,289,133 | 9/1981 | Rothluss | 227/19 X |
| 4,290,542 | 9/1981 | Fedotov et al. | 227/155 |
| 4,304,236 | 12/1981 | Conta et al. | 128/325 |
| 4,354,628 | 10/1982 | Green | 227/19 |
| 4,383,634 | 5/1983 | Green | 227/19 |
| 4,402,444 | 9/1983 | Green | 227/19 |
| 4,429,695 | 2/1984 | Green | 128/305 |
| 4,475,679 | 10/1984 | Fleury, Jr. | 227/DIG. 1 |
| 4,522,327 | 6/1985 | Korthoff et al. | 227/19 |
| 4,530,453 | 7/1985 | Green | 227/19 |
| 4,580,712 | 4/1986 | Green | 227/DIG. 1 |

FOREIGN PATENT DOCUMENTS 927936 6/1963 United Kingdom .
1158113 7/1969 United Kingdom .

Primary Examiner—Paul A. Bell
Attorney, Agent, or Firm—Kenyon & Kenyon

[57] ABSTRACT

Apparatus for substantially simultaneously applying a plurality of surgical fasteners to body tissue includes means for preventing all of the fasteners from reaching peak formation force at the same time in order to reduce the maximum force required to operate the apparatus.

8 Claims, 14 Drawing Sheets

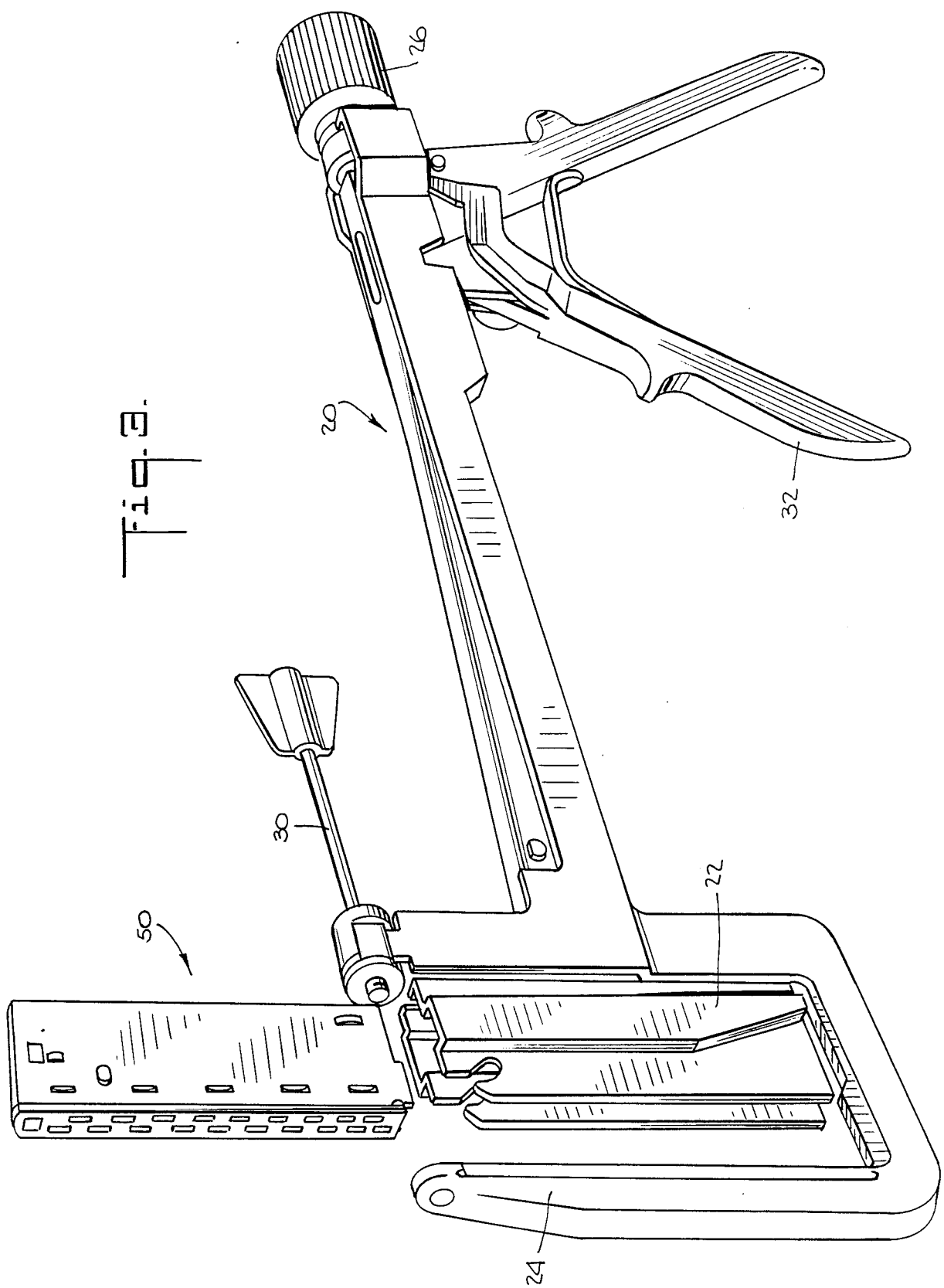

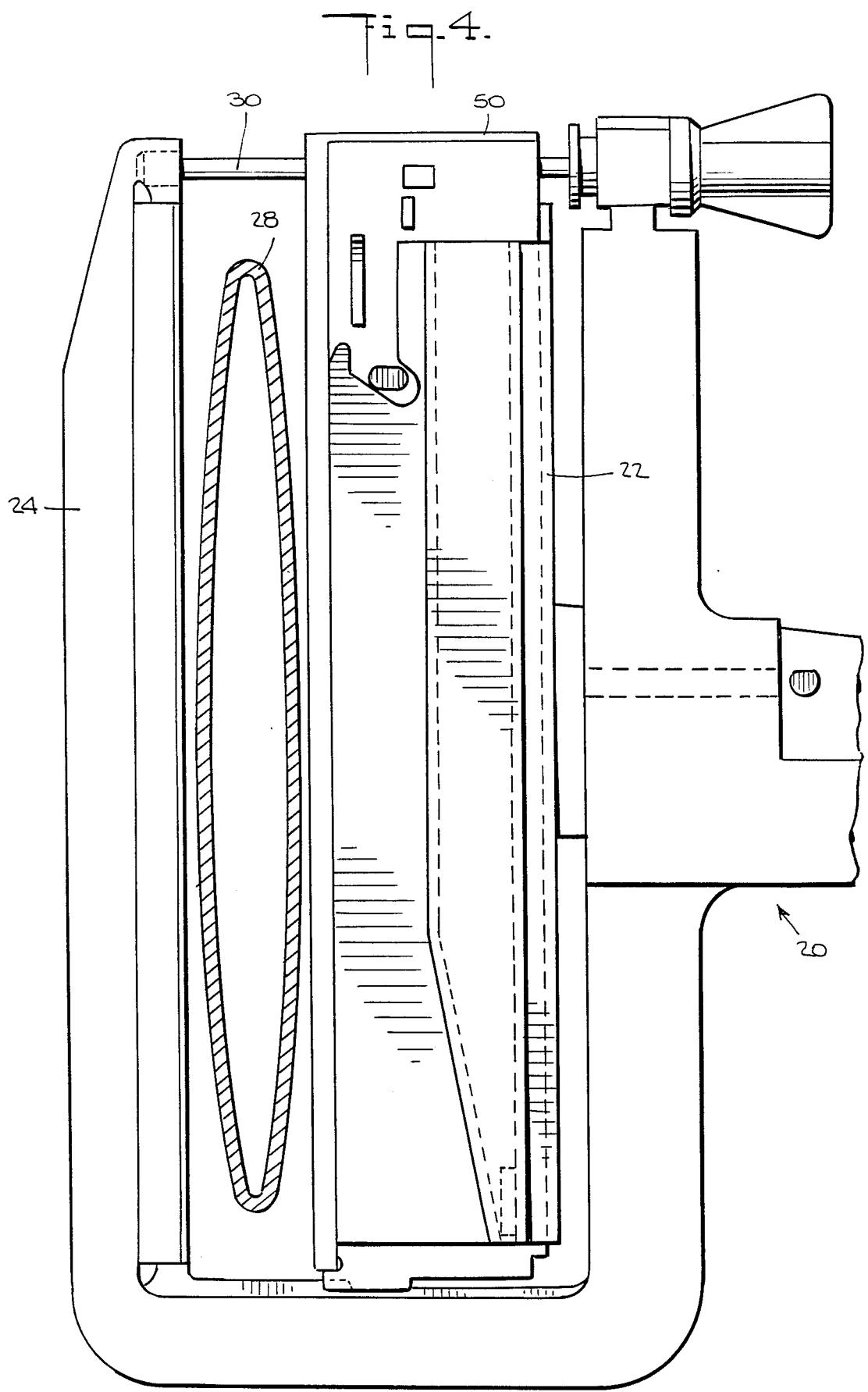

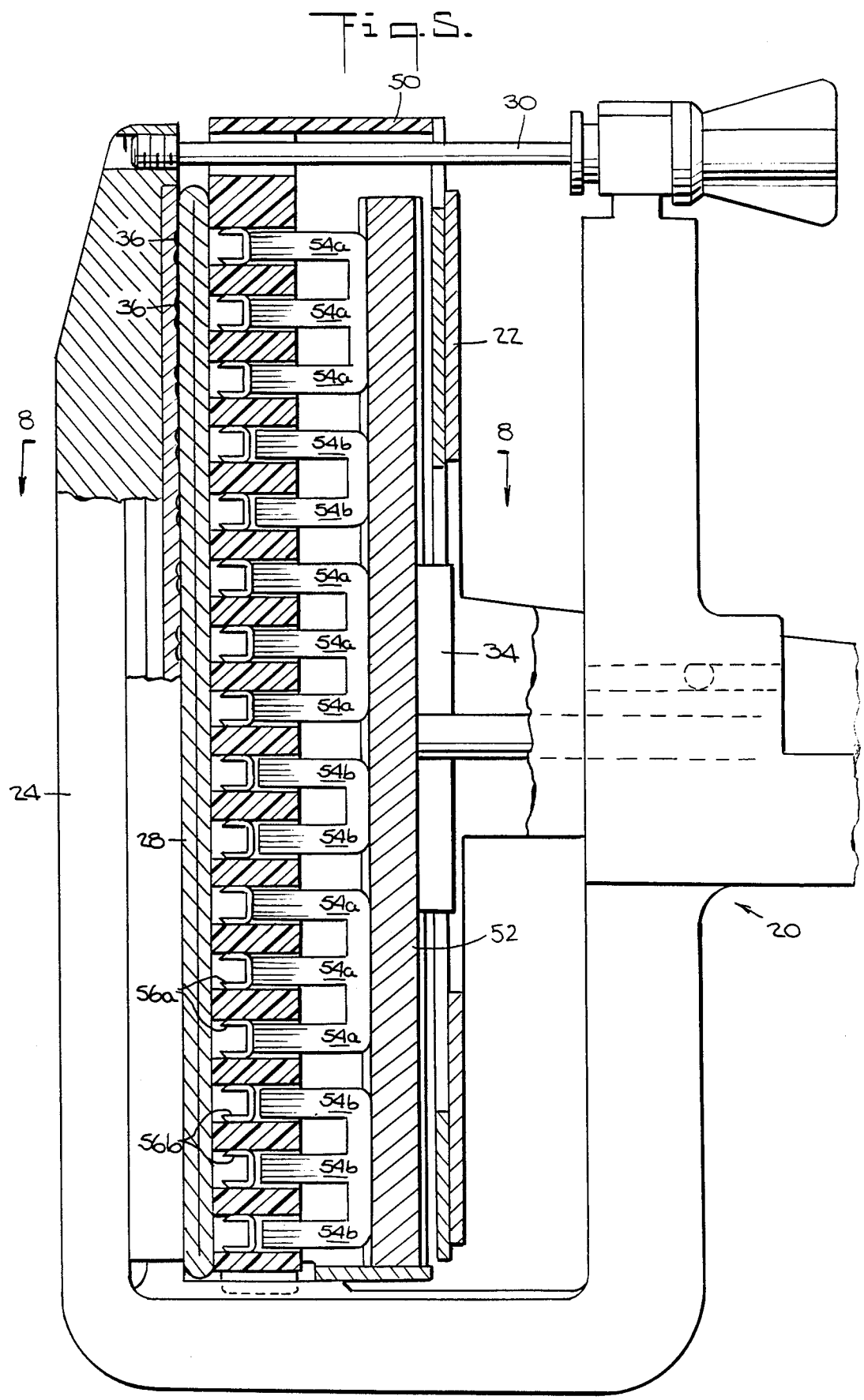

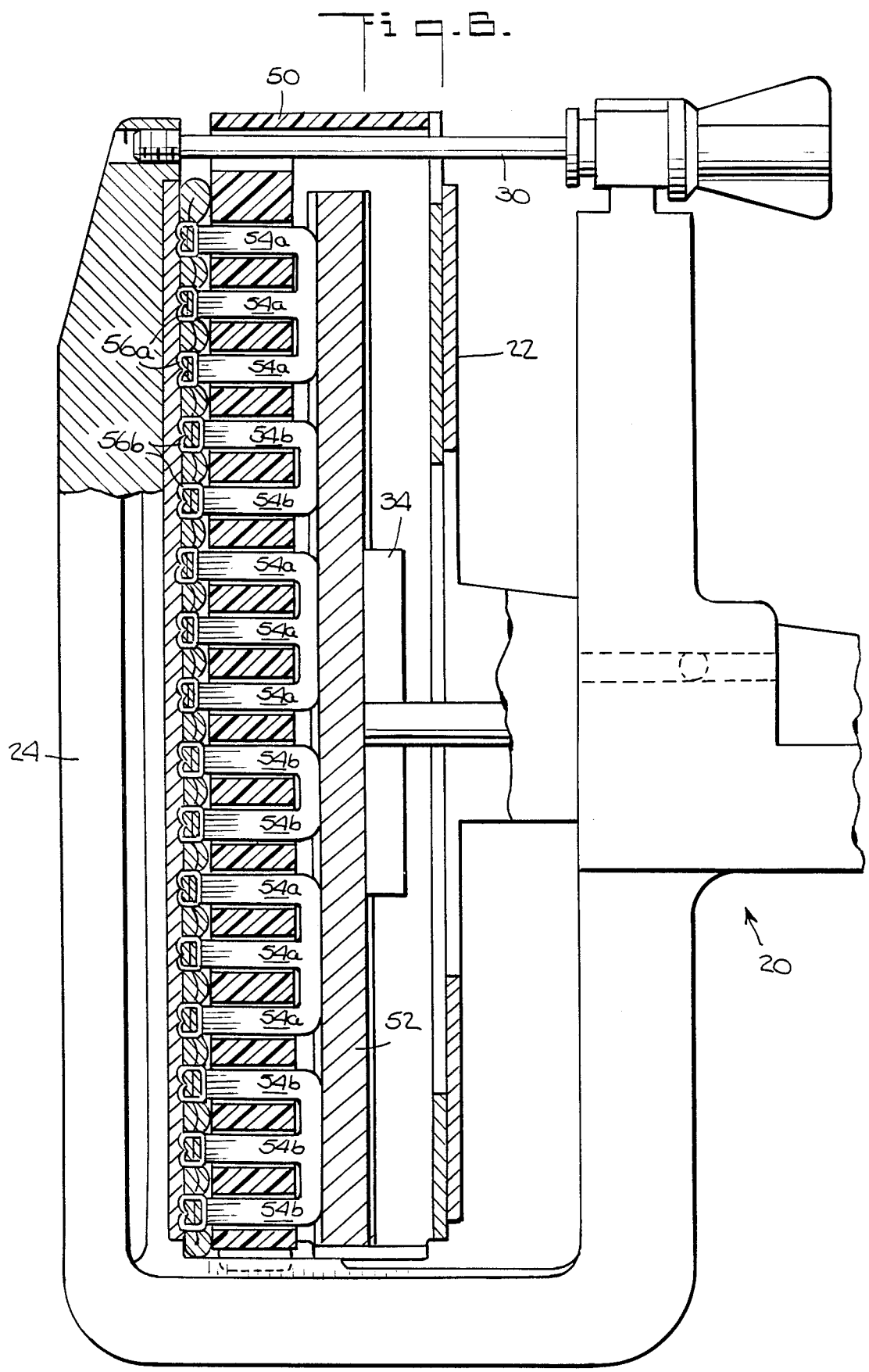

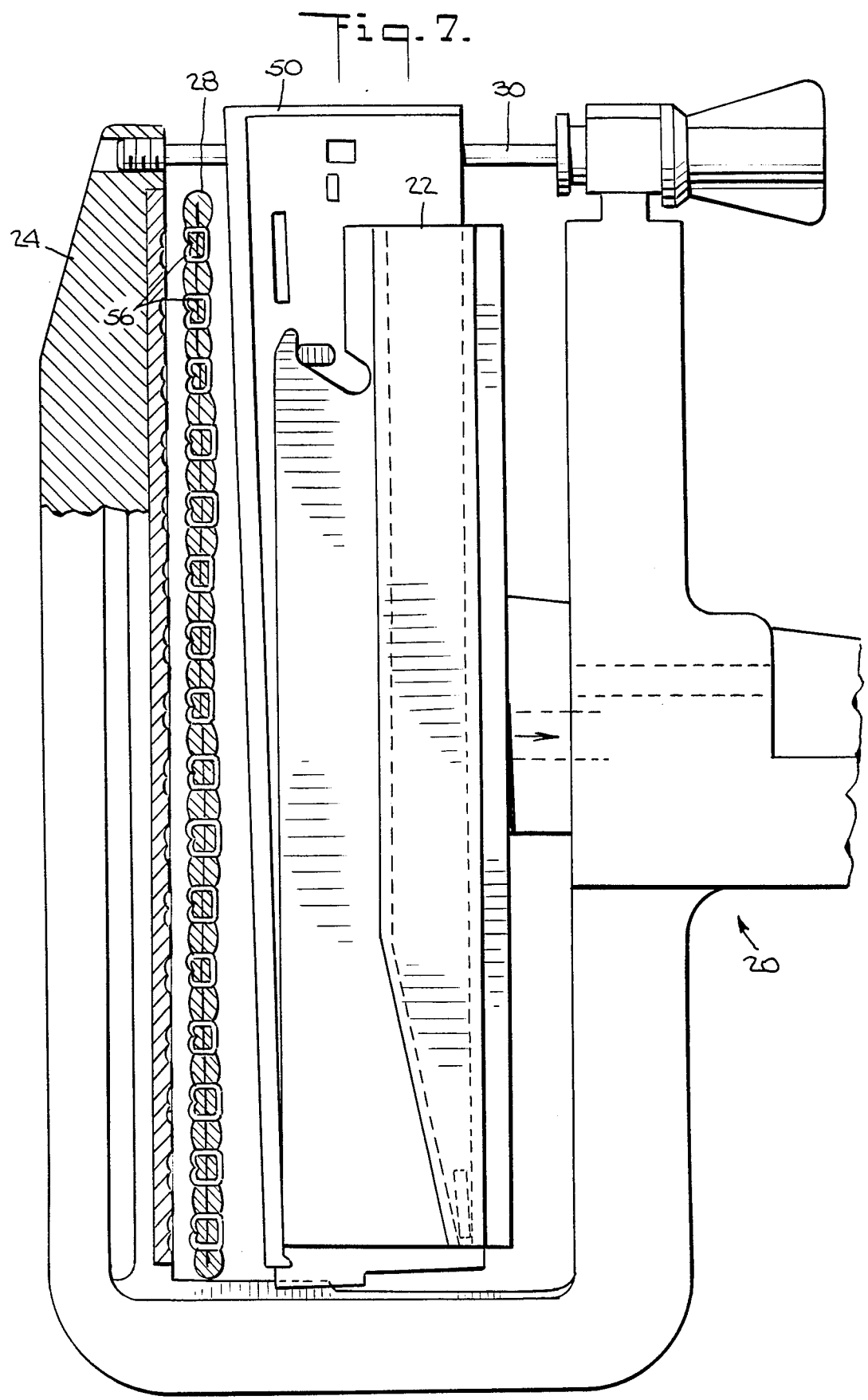

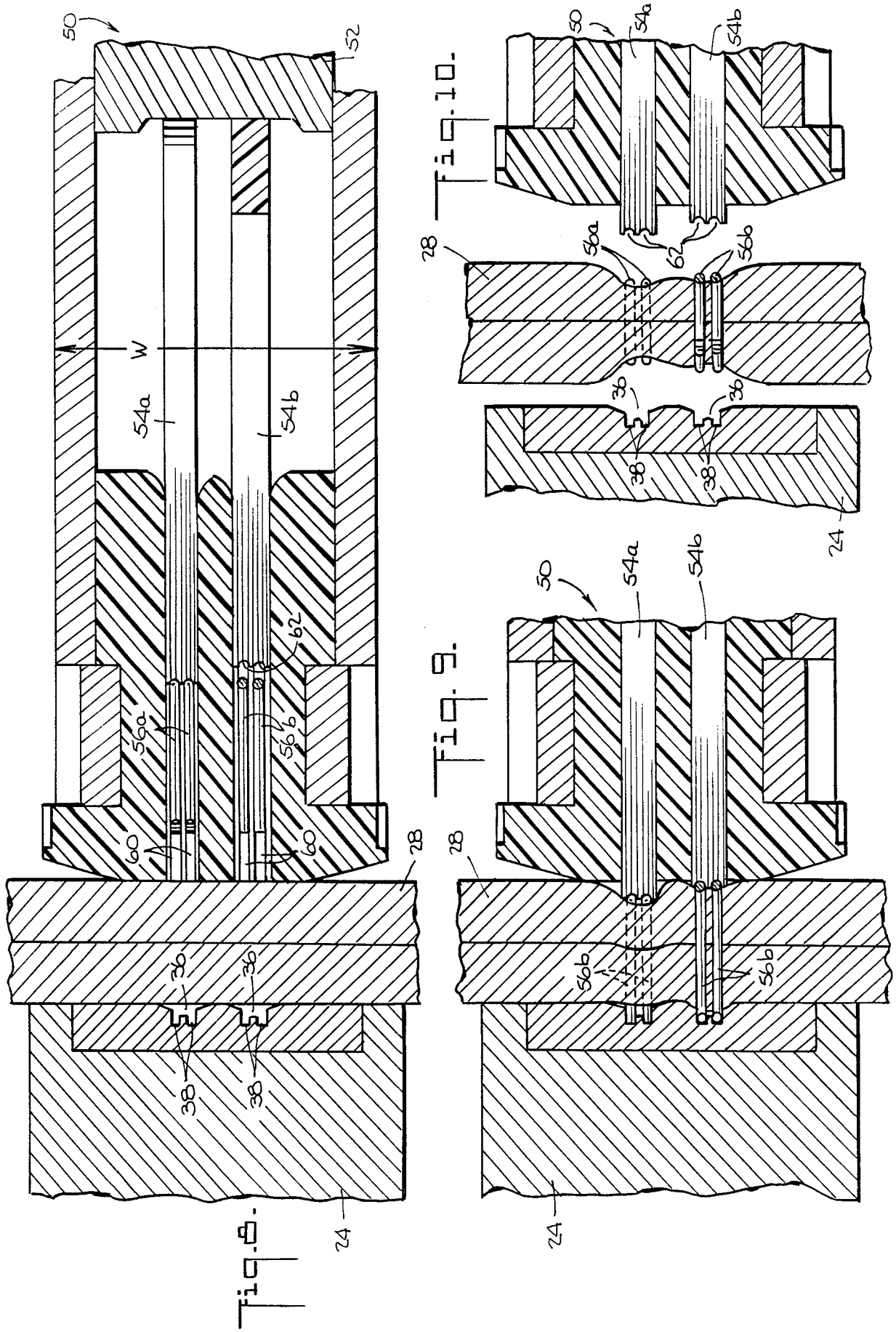

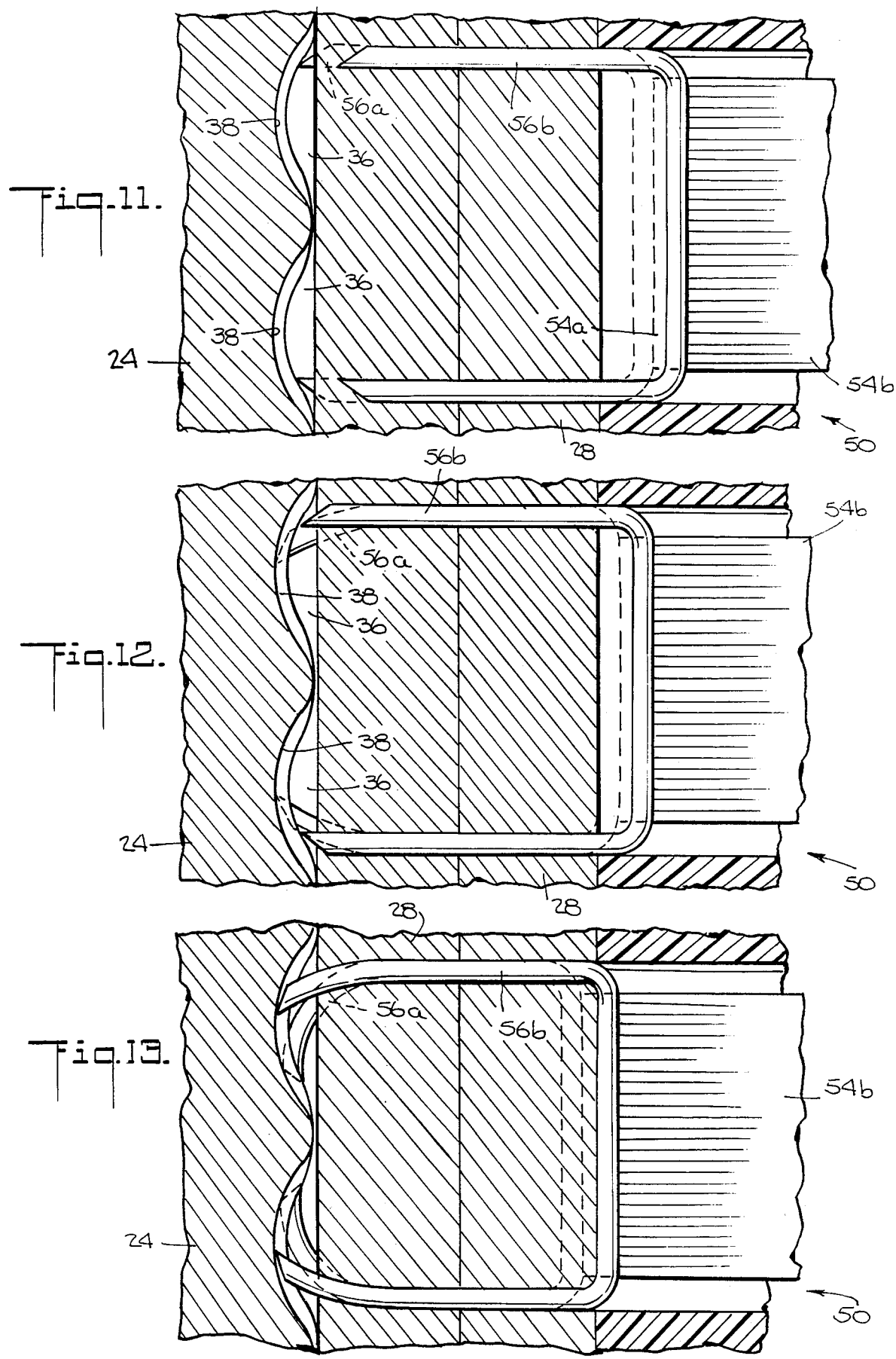

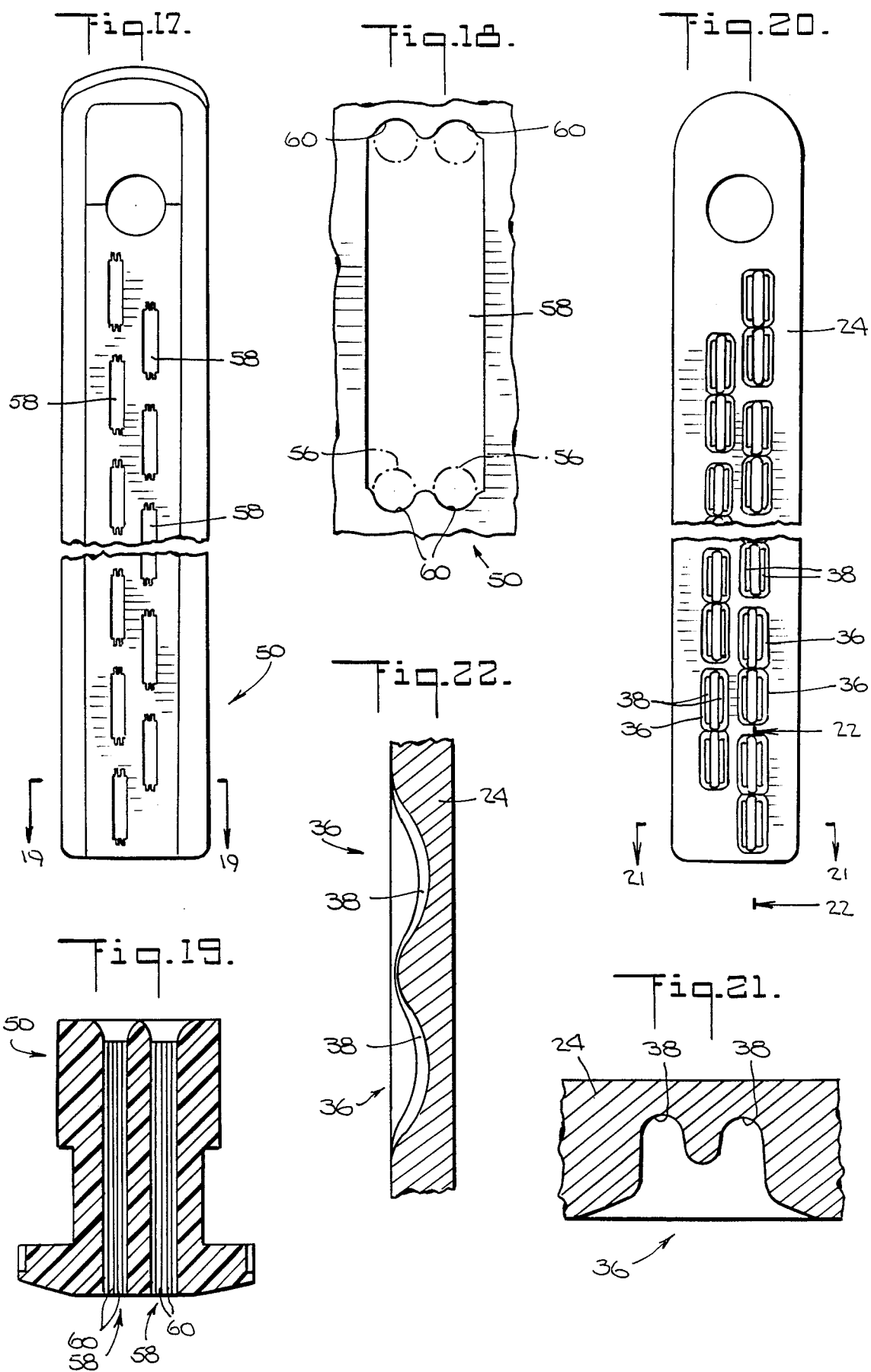

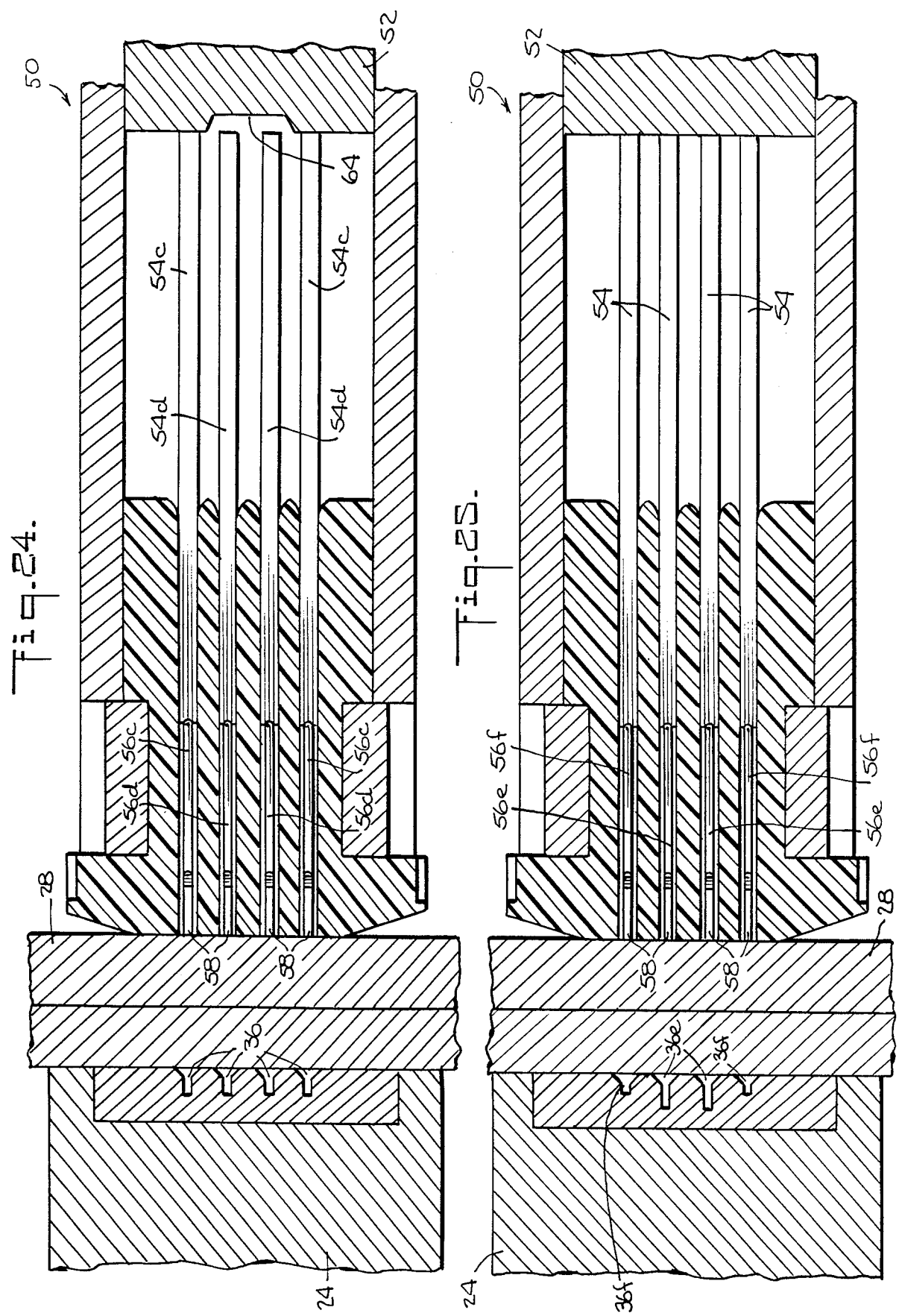

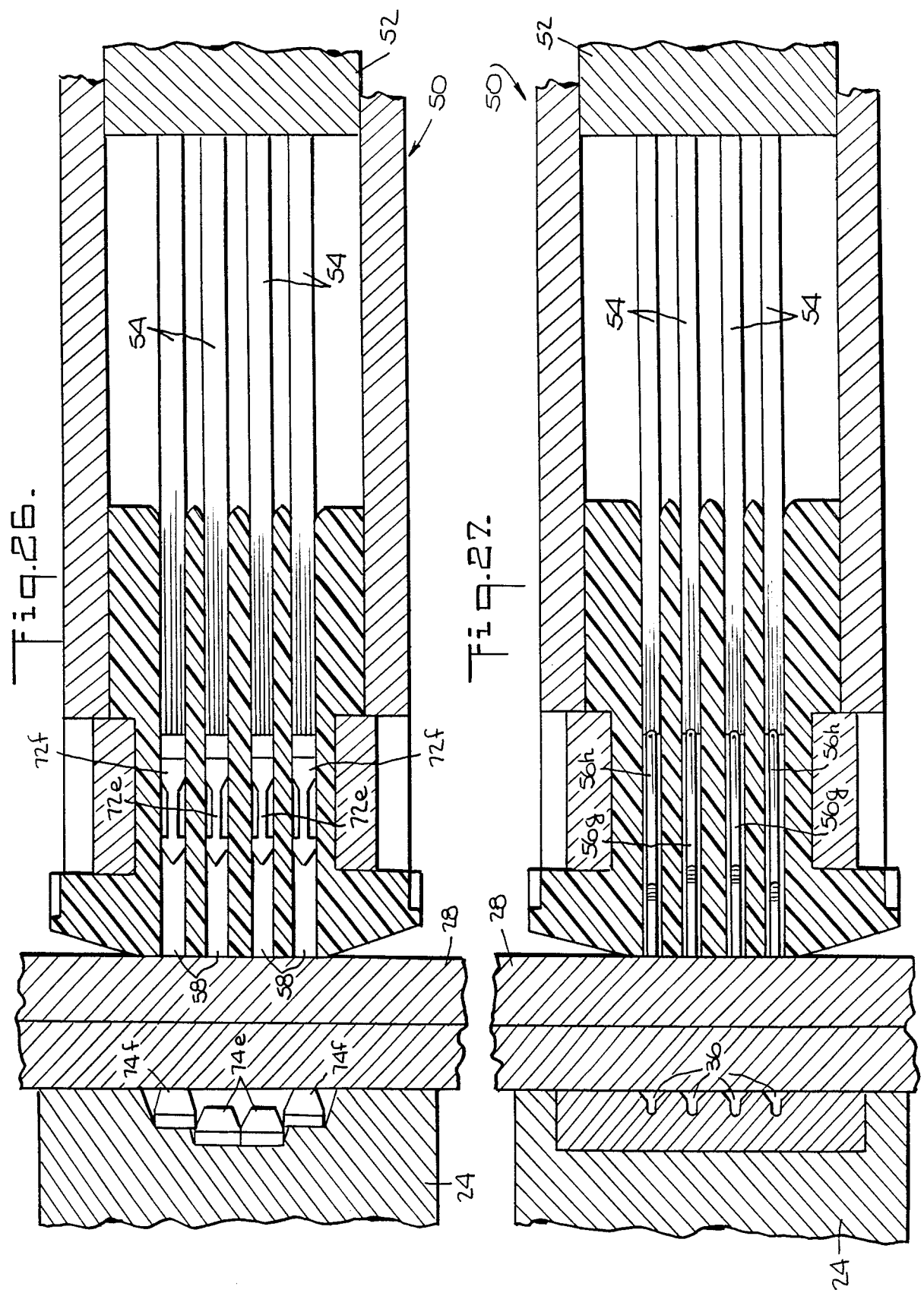

SURGICAL FASTENER APPLYING APPARATUS

BACKGROUND OF THE INVENTION

This application is a continuation-in-part of application Ser. No. 662,679, filed Oct. 19, 1984 now U.S. Pat. No. 4,580,712.

This invention relates to surgical fastener applying apparatus, and more particularly to surgical fastener applying apparatus of the type that applies a plurality of surgical fasteners simultaneously or substantially simultaneously.

Among the known types of surgical fastener applying instruments are several that apply a plurality of surgical fasteners simultaneously or substantially simultaneously. For example, Hirsch et al. U.S. Pat. No. 3,275,211 shows apparatus for simultaneously applying a plurality of metal surgical staples in a linear array. As another example, Conta et al. U.S. Pat. No. 4,304,236 shows apparatus for simultaneously applying a plurality of metal surgical staples in a circular array.

In the present context, a surgical fastener applying instrument is said to apply a plurality of surgical fasteners "simultaneously" or "substantially simultaneously" if, during at least some portion of the fastener applying stroke of the apparatus, all of the fasteners are simultaneously in motion relative to the fastener holding portion of the apparatas. Apparatus which simultaneously or substantially simultaneously applies a plurality of surgical fasteners is therefore different from apparatus such as that shown in Green U.S. Pat. No. 4,429,695 which completes the application of some surgical fasteners before the application of other fasteners has begun. Apparatus of the type shown in the Green '695 patent is not of interest in relation to the present invention.

The fasteners applied by instruments of the types shown in the above-mentioned Hirsch et al. and Conta et al. patents need not be metal surgical staples. For example, Green U.S. Pat. No. 4,506,671 shows two-part surgical fasteners made of resinous materials which can be used as an alternative to metal surgical staples. Such two-part fasteners typically have a fastener part and a retainer part. The prongs of the fastener part are driven part way through the tissue to be fastened, whereupon the ends of the prongs interlock with the associated retainer part to secure the tissue. As used herein, the term "surgical fastener" is generic to metal staples, two-part resinous fasteners, and the like.

Most of the known surgical fasteners are characterized by a relatively sharp peak force requirement during application. For example, relatively little force is required to push the sharply pointed legs of metal surgical staples through tissue. However, when the ends of the staple legs reach the anvil of the stapler, a relatively large force is required to begin to bend or crimp the staple legs. Once the staple legs have begun to bend, the force required to continue bending the staple legs is substantially less than the force required to initiate bending. Similarly, the force required to push the prongs of two-part fasteners through tissue is typically substantially less than the force required to cause the ends of the prongs to interlock with the retainer part of the fastener.

As used herein, the term "formation force" refers to the force required to apply a surgical fastener, and the term "peak formation force" refers to the maximum force required during application of a surgical fastener. In general, a surgical fastener reaches its peak formation force when it first contacts or engages the associated "fastener forming means", i.e., the anvil of the stapler in the case of metal staples or the retainer part of the fastener in the case of two-part resinous fasteners.

Several of the known surgical fastener applying instruments simultaneously apply approximately 30 surgical fasteners. For some surgical procedures, there is interest in simultaneously applying even more than 30 fasteners (e.g., 60 or more fasteners). Because all of these fasteners are applied simultaneously, all of the fasteners reach their peak formation force simultaneously, thereby requiring the surgeon to apply a very large force to the fastener applying apparatus. This may make the apparatus relatively difficult to operate. In addition, the need to provide structures which can receive and transmit such large forces may increase the size, cost, and complexity of the fastener applying apparatus. The size of the apparatus may also undesirably increase as a result of the application of an increased number of fasteners.

In view of the foregoing, it is an object of this invention to improve surgical fastener applying apparatus of the type which simultaneously applies a large number of surgical fasteners.

It is another object of this invention to reduce the maximum force required to operate surgical fastener applying apparatus of the type which simultaneously applies a plurality of surgical fasteners.

It is still another object of this invention to reduce the size of the apparatus required to apply a large number of surgical fasteners.

SUMMARY OF THE INVENTION

These and other objects of the invention are accomplished in accordance with the principles of the invention by including in surgical fastener applying apparatus of the type described above means for causing at least one of the fasteners to reach peak formation force before at least one other fastener reaches peak formation force. In general, this is accomplished by including in the apparatus means for causing at least one fastener to engage the fastener forming means before at least one other fastener engages the fastener forming means. For example, in apparatus for substantially simultaneously applying a plurality of metal surgical staples, the above-mentioned means causes at least one staple to contact the anvil of the stapler before at least one other staple contacts the anvil. The staples may contact the anvil successively, or the staples may be grouped in two or more groups so that the groups contact the anvil successively. In the case of apparatus which substantially simultaneously applies a plurality of two-part resinous fasteners, the above-mentioned means causes at least one fastener part to interlock with its associated retainer part before at least one other fastener part interlocks with its associated retainer part. Once again, the fastener and retainer parts may interlock successively, or the fasteners may be grouped in two or more groups so that the groups interlock successively.

The invention reduces the maximum force required to apply a given number of surgical fasteners because it prevents all of the fasteners from reaching their peak formation force at the same time.

Various embodiments of the invention have been developed. In a first embodiment, some of the fastener pushers are shorter than other pushers so that the fasteners associated with the shorter pushers are retarded relative to the other fasteners. In a second embodiment, the structure which drives the pushers is stepped so that some pushers are retarded relative to other pushers. In a third embodiment, the anvil structure associated with some fasteners (staples) is recessed relative to the anvil surface associated with other fasteners so that the fasteners associated with the more recessed anvil surface reach that surface after the other fasteners reach the less recessed anvil surface. In the two-part fastener equivalent of the third embodiment, the retainer parts associated with some fastener parts are recessed relative to the retainer parts associated with the other fastener parts. In a fourth embodiment, the fasteners themselves vary in size so that they do not all reach peak formation force at the same time. In the case of metal staples, for example, the legs of some staples are shorter than the legs of other staples so that the staples with longer legs contact the anvil before the staples with shorter legs. Similarly, the legs of the fastener parts of some two-part fasteners can be made shorter than other fastener part legs so that the fastener parts with longer legs interlock with their associated retainer parts before the fastener parts with shorter legs interlock with their associated retainer parts. In a fifth embodiment, the structure that pushes the fasteners toward the fastener forming means (i.e., the anvil or retainer parts) is angled slightly so that some fasteners are pushed slightly ahead of other fasteners.

In accordance with another aspect of the invention, the size of apparatus for applying a large number of surgical fasteners can be reduced by placing two fasteners in each fastener holding aperture in the apparatus. The apertures are shaped to keep the fasteners in each aperture separate from one another and to prevent them from becoming entangled with one another as they are driven from the aperture and thereby applied to tissue.

Further features of the invention, its nature and various advantages will be more apparent from the accompanying drawings and the following detailed description of the invention.

BRIEF DESCRIPTION OF THE DRAWINGS

FIG. 3 is a perspective view of a first illustrative embodiment of the invention.

FIG. 4 is an elevational view of a portion of the apparatus of FIG. 3 showing an early stage in the operating cycle of that apparatus.

FIGS. 5-7 are views similar to FIG. 4 showing successive stages in the operating cycle of the apparatus of FIG. 3.

FIG. 8 is a cross-sectional view taken along the line 8—8 in FIG. 5.

FIGS. 9 and 10 are views similar to FIG. 8 corresponding, respectively, to the operating cycle stages shown in FIGS. 6 and 7.

FIGS. 11-16 are detailed sectional views showing successive stages in the formation of representative staples in the apparatus of FIG. 3.

FIG. 17 is an elevational view of the front of the staple holding cartridge in the apparatus of FIG. 3.

FIG. 18 is an enlargement of a portion of FIG. 17.

FIG. 19 is a cross sectional view taken along the line 19—19 in FIG. 17.

FIG. 20 is an elevational view of the anvil in the apparatus of FIG. 3.

FIGS. 21 and 22 are cross sectional views taken respectively along the lines 21—21 and 22—22 in FIG. 20.

FIG. 24 is a view similar to FIG. 8 showing another alternative embodiment of the invention.

FIG. 25 is another view similar to FIG. 8 showing yet another alternative embodiment of the invention.

FIG. 26 is another view similar to FIG. 8 showing still another alternative embodiment of the invention.

FIG. 27 is another view similar to FIG. 8 showing yet another alternative embodiment of the invention.

DETAILED DESCRIPTION OF THE INVENTION

Figure 1:
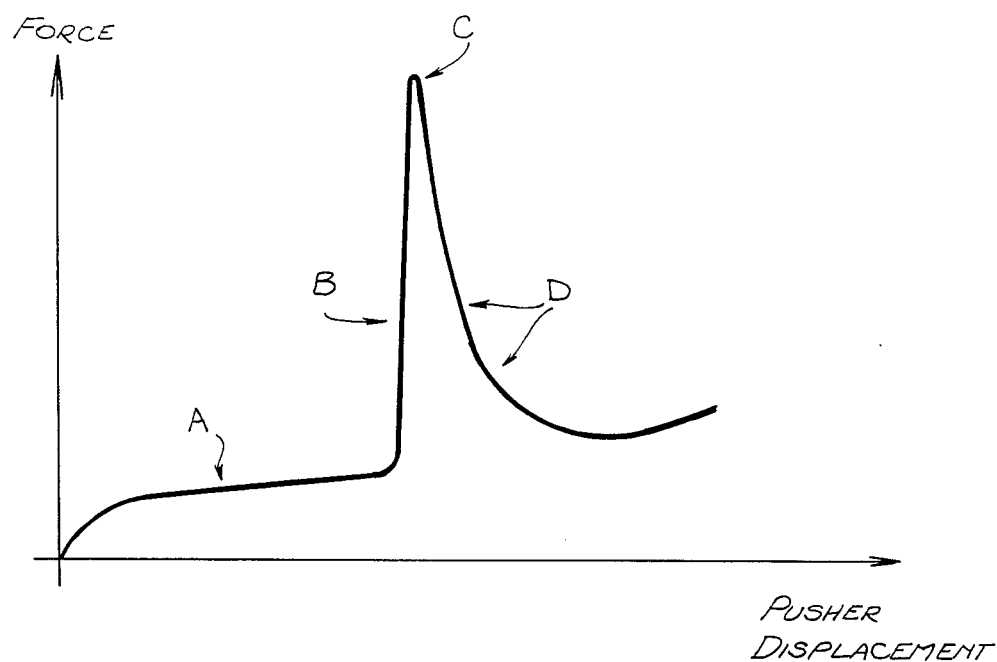
FIGS. 1 and 2 are force diagrams useful in explaining the principles of the invention.

In FIG. 1, the force required to apply a typical metal surgical staple is plotted as a function of the displacement of the associated staple pusher. (See also FIG. 59 of Green et al. U.S. Pat. No. 3,494,533.) The initial force requirement (region A) is relatively low as the pusher pushes the sharply pointed legs of the staple through the tissue. As soon as the ends of the staple legs contact the anvil of the stapler, however, the force requirement increases very rapidly (region B) to the peak formation force C, i.e., the force required to initiate bending of the staple legs. Once bending has been initiated, the force requirement decreases rapidly again (region D).

The formation force requirement for the typical two-part resinous surgical fastener (FIG. 2) is generally similar to that described above. Initially (region A), relatively little force is required to push the sharply pointed ends of the fastener part prongs through the tissue. However, when the latches on the fastener part prongs contact the latches on the associated retainer part, the formation force requirement increases very rapidly (region B) to the peak formation force C, i.e., the force required to cause the latches on the fastener and retainer parts to interlock. Thereafter (region D), the force requirement drops off rapidly again.

Figure 2:
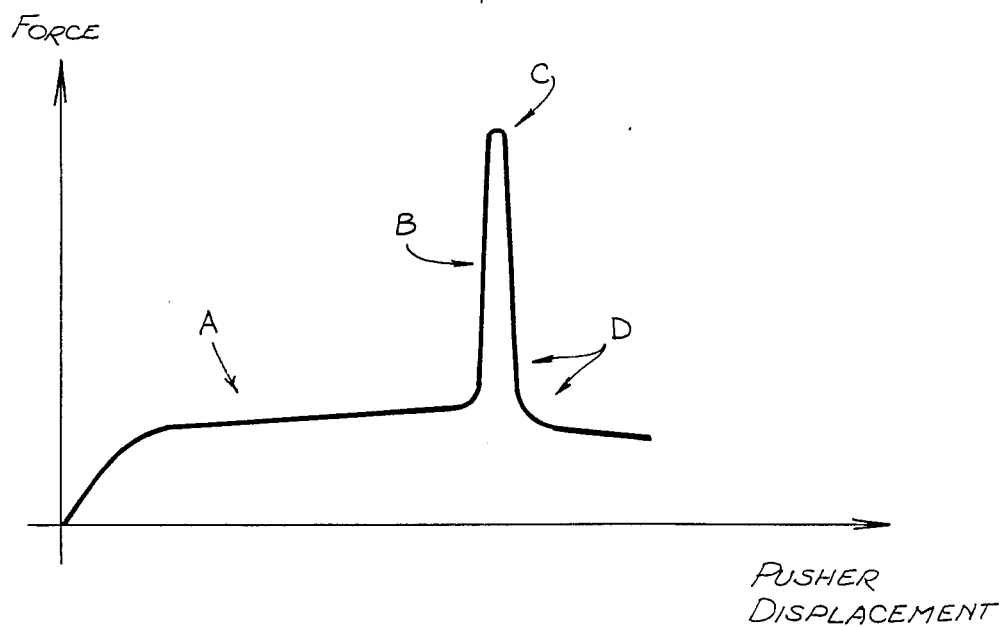

In accordance with this invention, apparatus for substantially simultaneously applying a plurality of surgical fasteners characterized by formation force curves like those shown in FIGS. 1 and 2 is constructed so that all of the fasteners do not reach their peak formation force C at the same time. In particular, the surgical fastener applying apparatus of this invention is constructed so that at least some of the fasteners reach their peak formation force C while at least some other fasteners are still at their relatively low initial formation force A, and so that the fasteners that are first to reach peak formation force have returned to relatively low formation force D when the fasteners that are last to reach peak formation force reach their peak formation force C. In this way, the maximum force required to operate the fastener applying apparatus of this invention is substantially less than it would be if all of the fasteners reached peak formation force at the same time.

A first illustrative embodiment of the invention is shown in FIGS. 3-22 in the context of surgical fastener applying apparatus of the type shown in commonly assigned, co-pending Green U.S. patent application Ser. No. 598,461, filed Apr. 9, 1984, which is hereby incorporated by reference herein for background information not essential for understanding or practicing the present invention. As shown in FIG. 3, this apparatus includes a reusable actuator 20 for removably receiving and actuating a disposable staple holding cartridge 50. When cartridge 50 is placed in cartridge holder 22, cartridge holder 22 can be moved toward anvil 24 by rotation of clamp actuator 26 (compare FIGS. 4 and 5). The tissue 28 to be fastened is thereby clamped between cartridge 50 and anvil 24. Alignment pin 30 is pushed through cartridge 50 into anvil 24 to help register and align elements 50 and 24 and to help confine tissue 28 between those elements.

When tissue 28 is fully clamped as shown in FIG. 5, handle 32 (FIG. 3) is pivoted to the rear to drive fastener actuator bar 34 in the distal direction as shown in FIG. 6. Fastener actuator bar 34 enters the rear of cartridge 50 and pushes pusher driver 52 in the distal direction. This in turn pushes all of pushers 54a and 54b in the distal direction. Some of pushers 54 (i.e., those designated 54a) are slightly longer than the other pushers (i.e., those designated 54b). (Pushers 54a and 54b are joined together in groups of two or three for reasons (such as reduction of the number of separate parts in the apparatus) having nothing to do with the present invention.) The difference in length of pushers 54a and 54b is typically relatively small (e.g., 0.008–0.012 inches) and is exaggerated in the accompanying drawings to better illustrate the invention.

When pushers 54 are pushed in the distal direction as described above, they push staples 56 toward anvil 24 as shown progressively in FIGS. 11–16. Anvil 24 has pockets 36 for clinching staples 56 in the conventional manner. (In order to facilitate comparison of the progress of staples 56a (associated with relatively long pushers 54a) with the progress of staples 56b (associated with relatively short pushers 54b), a staple 56b is superimposed on a staple 56a in FIGS. 11–16, although in that respect FIGS. 11–16 are not true views of the apparatus.) As shown in FIG. 11, the ends of the legs of staples 56a reach the surface of anvil 24 before the ends of the legs of staples 56b reach that surface. Accordingly, staples 56a reach peak formation force C (FIG. 1) while staples 56b are still in relatively low initial formation force region A. As pushers 54 continue to move in the distal direction, the ends of the legs of staples 56a begin to bend inwardly as shown in FIG. 12, and the ends of the legs of staples 56b continue to move toward the surface of anvil 24. Accordingly, staples 56a pass peak formation force C and enter reduced formation force region D before staples 56b reach peak formation force C.

Continued distal motion of pushers 54 causes staples 56a to continue to bend, and causes staples 56b to reach peak formation force C and to begin to bend as shown in FIG. 13. Accordingly, when staples 56b reach peak formation force C, staples 56a are already well past peak formation force and into reduced formation force region D.

Figure 14:
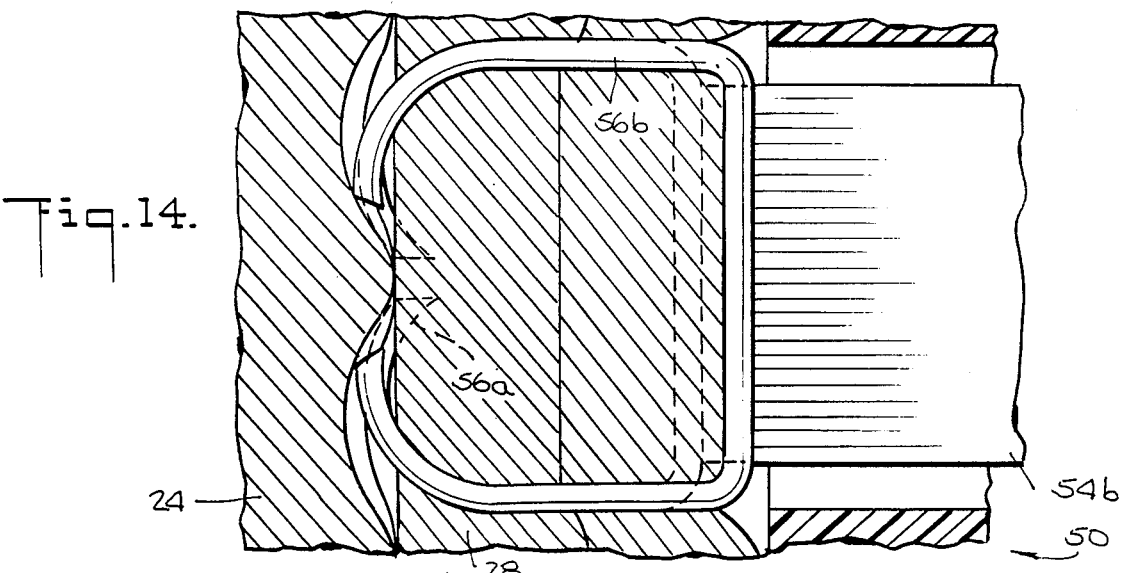
Figure 15:
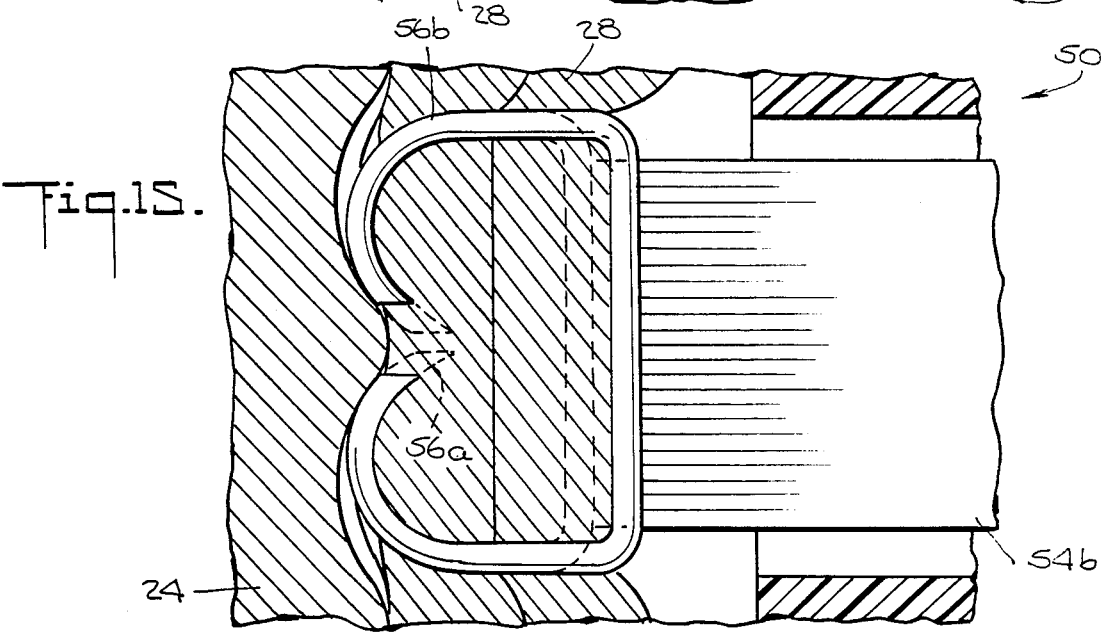
Figure 16:
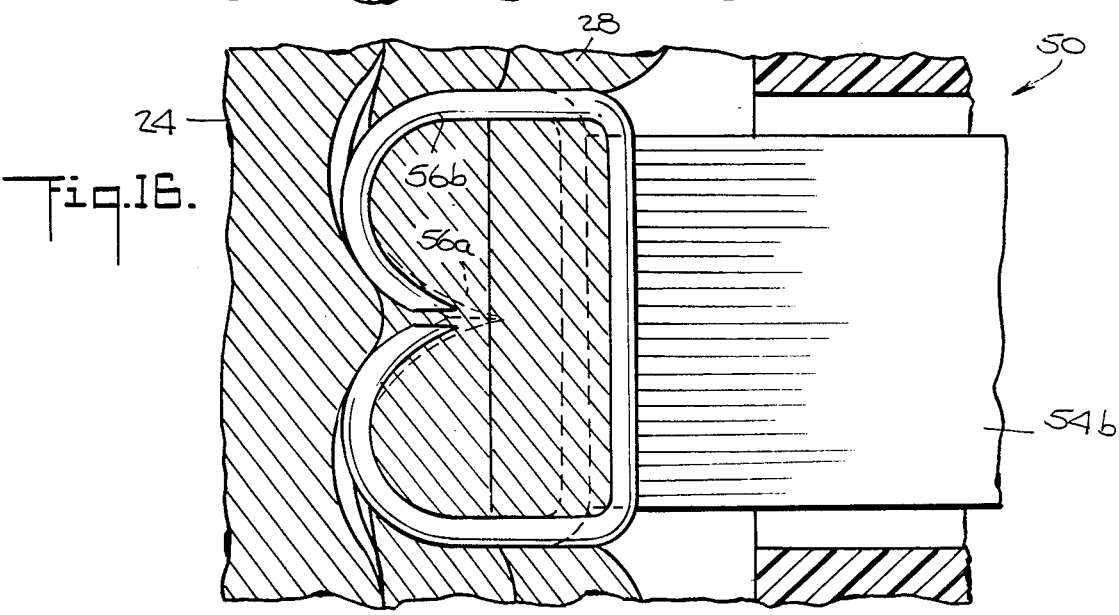

Still further distal motion of pushers 54 causes staples 56a and 56b to continue to bend as shown in FIGS. 14–16. Because pushers 54a are slightly longer than pushers 54b, staples 56a are clinched slightly more than staples 56b at the end of the staple applying stroke of the apparatus as shown in FIG. 16. This does not adversely affect the resulting staple array.

When all of staples 56 have been fully clinched as shown in FIG. 16, the stapling operation is complete. Handle 32 is accordingly released and clamp actuator 26 is rotated to proximally retract cartridge holder 22 and cartridge 50. This releases the clamping pressure on tissue 28 as shown in FIG. 7. The apparatus can be removed from the tissue when alignment pin 30 is proximally retracted.

Because staples 56a pass through peak formation force C before staples 56b, the maximum force required to operate the apparatus is substantially less than it would be if all of staples 56 passed through peak formation force C at the same time.

In accordance with another aspect of the invention illustrated by the embodiment of FIGS. 3–22, the width W (FIG. 8) of cartridge 50 and anvil 24 can be kept relatively small even though a large number of fasteners is applied by the apparatus by using two staples 56 in each cartridge slot 58 instead of one staple in each slot as is customary. The structure facilitating the use of two staples 56 in each cartridge slot 58 is best seen in FIGS. 8–10 and 17–22. As shown in FIG. 18, the opposite ends of each cartridge slot 56 have two laterally spaced grooves 60 parallel to the axis along which staples 56 are driven. Each groove 60 receives and guides one leg of one of the two staples 56 in the slot. The distal end of each pusher 54 also has two parallel, laterally spaced grooves 62 (see FIGS. 8–10). Each groove 62 receives the backspan of a respective one of the two staples in the associated slot 58. Each of anvil pockets 36 also has two laterally spaced grooves 38 parallel to grooves 62 (see FIGS. 8–10 and 20–22). Each of grooves 38 receives and guides the end of one leg of one of the two staples driven into pocket 36 in order to clinch the staples. Thus although two staples 56 are provided in each slot 58, the foregoing structure keeps the staples in each slot separate from one another and prevents them from becoming entangled with one another as they are driven.

Although two staples 56 are employed in each slot 58 in the embodiment shown in FIGS. 3–22, those skilled in the art will appreciate that this is not necessarily the case, and that a single staple 56 could be used in each slot 58 if desired. See also the embodiments shown in FIGS. 24–27 (discussed below) in which the same number of fasteners are employed as in the embodiment of FIGS. 3–22, but in which each fastener has its own slot 58.

Figure 23:
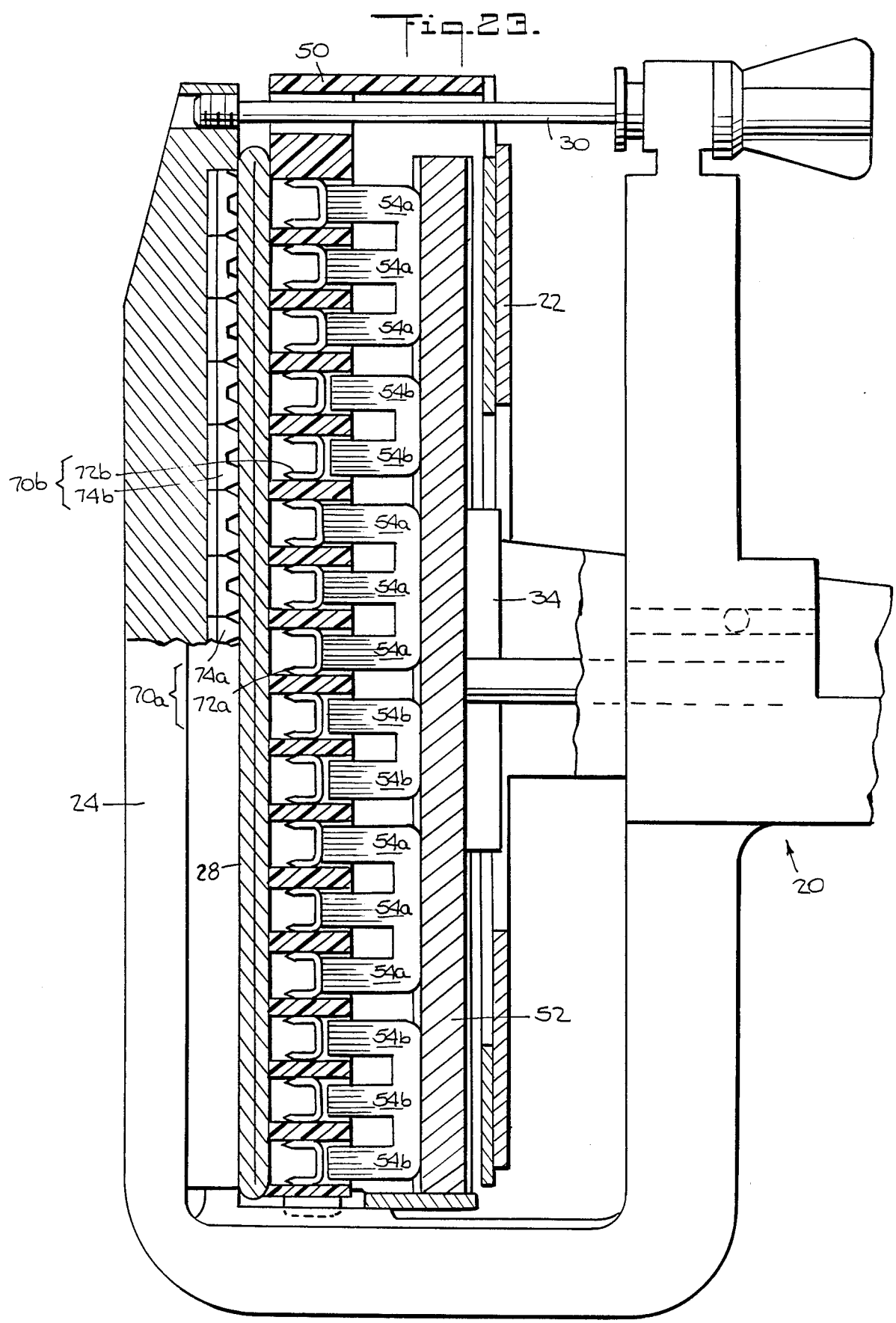
FIG. 23 is a view similar to FIG. 5 showing an alternative embodiment of the invention.

Those skilled in the art will also recognize that two-part resinous surgical fasteners of the type shown, for example, in Green U.S. Pat. No. 4,506,671 can be substituted for metal surgical staples 56 in the embodiment shown in FIGS. 3–22. This is illustrated by FIG. 23, which is similar to FIG. 5 but shows the apparatus with two-part resinous fasteners 70 in place of metal surgical staples 56. The fastener parts 72 of fasteners 70 replace staples 56. The retainer parts 74 of fasteners 70 replace anvil pockets 36. In other respects the construction and operation of the apparatus of FIGS. 23 can be generally similar to the construction and operation of the appratus of FIGS. 3–22. Because pushers 54a are slightly longer than pushers 54b which act as a means for driving the fastener parts 72 in staggered relation to the retainer parts 74, fastener parts 72a interlock with retainer parts 74a before fastener parts 72b interlock with retainer parts 74b. Accordingly, fasteners 70a reach peak formation force C (FIG. 2) while fasteners 70b are still in relatively low formation force region A, and fasteners 70b do not reach peak formation force C until fasteners 70a have passed through peak formation force C into reduced formation force region D. The maximum force required to operate the apparatus is therefore substantially less than it would be if all of fasteners 70 reached peak formation force C at the same time.

FIG. 24 shows another embodiment of the invention in which all of pushers 54 are the same length, but in which pusher driver 52 is notched, grooved, or otherwise stepped so that it begins to push some of pushers 54 (i.e., those designated 54c) before it begins to push other pushers (i.e., those designated 54d). FIG. 24 is similar to FIG. 8, but with the following differences: First, there is only one staple 56 in each cartridge slot 58. Second, there are four rows of cartridge slots 58 instead of only two rows as in FIG. 8. Third, all of pushers 54 are the same length. And fourth, pusher driver 52 contains a shallow central groove 64 so that when pushed in the distal direction, it contacts outer pusher rows 54c before it contacts inner pusher rows 54d. Accordingly, outer staple rows 56c are pushed slightly ahead of inner staple rows 56d and staples 56c pass through peak formation force C before staples 56d reach that force level. As in the embodiment of FIGS. 3–22, the maximum force required to operate the apparatus of FIG. 24 is substantially less than it would be if all of staples 56 reached peak formation force C at the same time. The depth of groove 64 can be similar to the difference between the lengths of pushers 54a and 54b in the embodiment of FIGS. 3–22. Those skilled in the art will appreciate that two-part resinous surgical fasteners of the type shown in FIG. 23 can be substituted for metal staples 56 in the embodiment of FIG. 24 if desired.

FIG. 25 shows yet another embodiment of the invention in which some of anvil pockets 36e are deeper than other anvil pockets 36f. In other respects the embodiment of FIG. 25 is similar to the embodiment of FIG. 24 except that pusher driver 52 is not grooved in FIG. 25. Because inner anvil pockets 36e are deeper than outer anvil pockets 36f, staples 56f contact anvil 24 before staples 56e. Accordingly, staples 56f pass through peak formation force C before staples 56e reach that force level. The maximum force required to operate the apparatus is therefore substantially less than it would be if all of staples 56 reached peak formation force C at the same time. The difference in depth between anvil pockets 36e and 36f can be similar to the difference between the lengths of pushers 54a and 54b in the embodiment of FIGS. 3–22.

Once again, those skilled in the art will appreciate that two-part resinous fasteners of the type shown in FIG. 23 can be substituted for metal staples 56 in the apparatus of FIG. 25 if desired. This is illustrated in FIG. 26. Inner retainer parts 74e are recessed relative to outer retainer parts 74f so that outer fasteners 70f interlock before inner fasteners 70e. In this way all of fasteners 70 do not pass through peak formation force C at the same time and the maximum force required to operate the apparatus is accordingly reduced.

Still another embodiment of the invention is shown in FIG. 27. In this embodiment (which is similar to the embodiment of FIG. 25 except that all of anvil pockets 36 are of the same depth), the legs of inner staples 56g are slightly shorter than the legs of outer staples 56h. Accordingly, outer staples 56h pass through peak formation force C before inner staples 56g pass through that force level. The result again is to reduce the maximum force required to operate the apparatus. The difference in staple leg length in this embodiment can be similar to the difference between the lengths of pushers 54a and 54b in the embodiment of FIGS. 3–22.

As in the case of the previously described embodiments, those skilled in the art will recognize that two-part resinous fasteners can be substituted for metal staples 56 in the embodiment of FIG. 27. In that event, the legs of the fastener parts of some of those fasteners are made longer than the legs of the fastener parts of the other fasteners in order to achieve operation similar to that described above in relation to FIG. 27.

Figure 28:
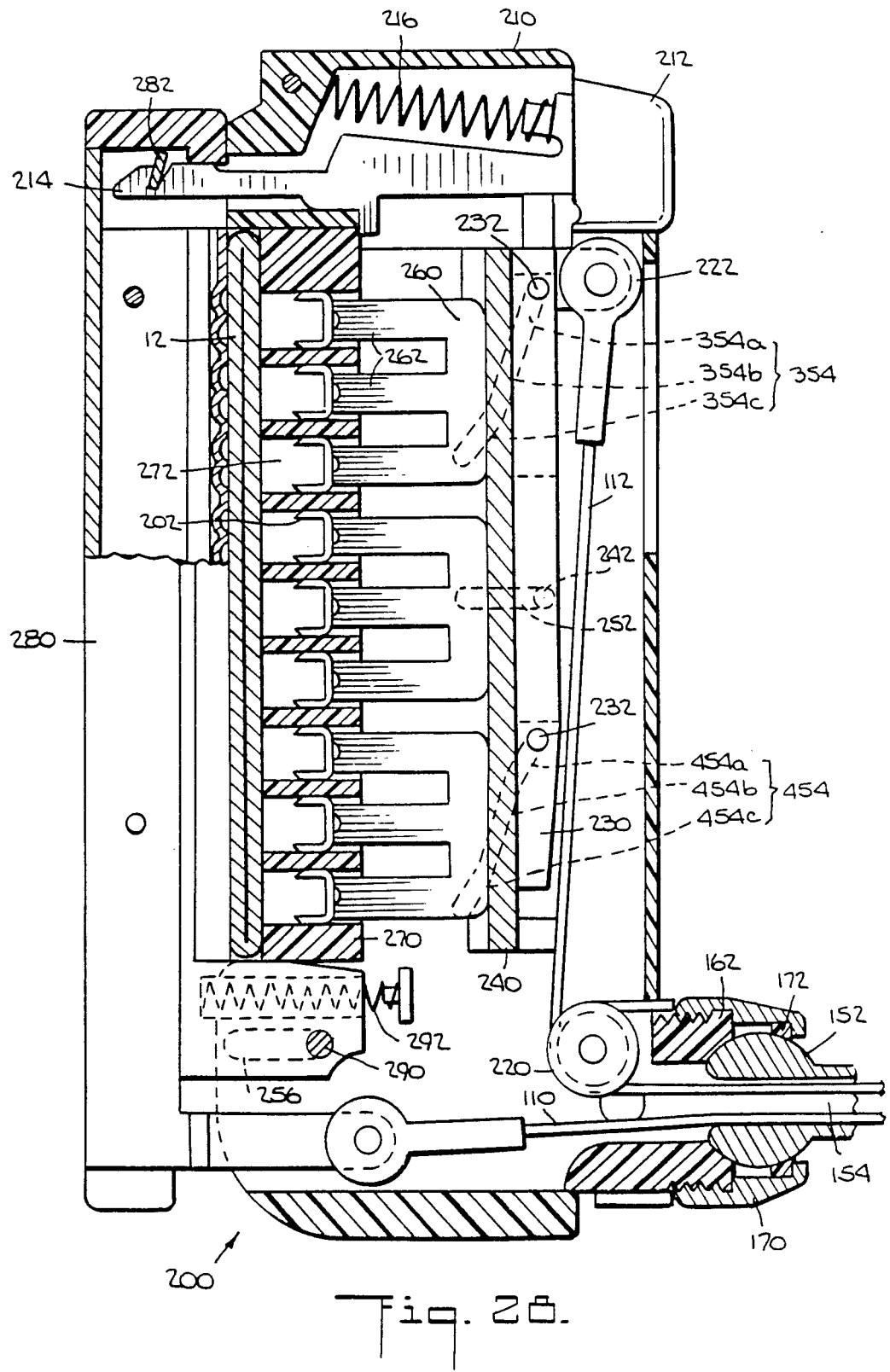
FIG. 28 is a view generally similar to FIG. 5 showing still another alternative embodiment of the invention.

Yet another alternative embodiment of the invention is shown in FIG. 28. This Figure is identical to FIG. 13 in commonly assigned, copending U.S. patent application Ser. No., 662,679, filed Oct. 19, 1984 now U.S. Pat. No. 4,580,712 issued Apr. 8, 1986. is hereby incorporated by reference herein for background information not essential for understanding or practicing the present invention. As described in detail in the aforementioned U.S. Pat. No. 4,580,712, staples 202 are driven in the distal direction when the proximal end of cable 112 is pulled in the proximal direction. This causes cam bar 230 to move down relative to pusher actuator member 240. As cam bar 230 moves down, it is also forced to move in the distal direction by cam follower pins 232 traversing cam slots 354 and 454. Because cam slots 354 and 454 have different shapes, the lower end of cam bar 230 initially moves more rapidly in the distal direction than the upper end of cam bar 230. This causes lower staples 202 to reach peak formation force C before upper staples 202 reach that force level. Although all of staples 202 are in motion at the same time relative to fastener holding part 210 (thereby satisfying the above definition of substantially simultaneous staple application), the staples reach and pass through peak formation force C progressively, from the bottom of the apparatus to the top as viewed in FIG. 28. Accordingly, at least some of staples 202 pass through peak formation force C before other staples reach that force level and the maximum force required to operate the apparatus is substantially less than it would be if all of staples 202 reached peak formation force C at the same time.

As in the previously described embodiments, two-part resinous fasteners of the type shown in FIG. 23 can be substituted for metal staples 202 in the embodiment of FIG. 28 if desired.

It will be understood that the embodiments shown and described herein are only illustrative of the principles of the invention, and that various modifications can be made by those skilled in the art without departing from the scope and spirit of the invention. For example, other structures for angling or inclining elements such as fastener actuator bar 34, pusher driver 52, and/or cam bar 230 to achieve a result similar to that described above in relation to FIG. 28 will be apparent to those skilled in the art.

I claim:

1. An apparatus for applying a plurality of surgical fasteners to body tissue comprising:
    a fastener carrying means having a plurality of fasteners therein;
    forming means opposite said fastener carrying means to form said fasteners after penetration through body tissue; and
    drive means including a longitudinal shaft and a drive bar located on a distal end of said shaft applying a positive drive force to said fasteners to drive said fastener from said fastener carrying means through the body tissue and toward said forming means;
    wherein at least one of said forming means and said drive means causes some of said fasteners to reach peak formation force before the remainder of said fasteners reach peak formation force.

2. An apparatus as set forth in claim 1 wherein said drive means further includes pusher means arranged between said drive bar and said fasteners, and wherein said pusher means associated with some of said fasteners are longer than said pusher means associated with the remainder of said fasteners.

3. An apparatus as set forth in claim 1, wherein said drive bar has a distal surface comprising first portions to contact said pushers associated with some of said fasteners, and second portions to contact said pushers associated with the remainder of said fasteners, and wherein said second portions are recessed relative to said first portions.

4. An apparatus as set forth in claim 1 wherein said forming means comprises an anvil having an anvil surface with staple-clinching grooves formed therein, wherein said fasteners comprise staples which are applied by clinching against said anvil surface in said staple-clinching grooves, and wherein said staple-clinching grooves associated with some of said staples are shallower than said staple-clinching grooves associated with the remainder of said staples.

5. An apparatus as set forth in claim 1 wherein said fasteners comprises resinous tissue-piercing parts, and said forming means includes resinous retainer parts releasably mounted therein, and wherein said resinous retainer means associated with the remainder of said fasteners are recessed on said forming means relative to said resinous retainer parts associated with some of said fasteners.

6. In an apparatus for applying a plurality of surgical fasteners to body tissue, the combination comprising:
a plurality of fasteners;
a fastener-carrying means;
forming means opposite said fastener-carrying means to form said fasteners after penetration through body tissue;
drive means including a longitudinal shaft and a drive bar located on a distal end thereof applying a positive drive force to said fasteners to drive said fastener from said fastener carrying means simultaneously though the body tissue and towards said forming means;
wherein some of said fasteners are longer than the remainder of said fasteners, said longer fasteners thereby contacting said forming means and reaching peak formation force before the remainder of said fasteners contact said forming means and reach peak formation force.

7. An apparatus as set forth in claim 6 wherein said fasteners comprise staples and wherein said forming means comprises an anvil having staple-clinching grooves formed therein.

8. An apparatus as set forth in claim 6 wherein said fasteners comprise resinous tissue-piercing parts, and wherein said forming means includes resinous retainer parts releasably mounted thereon and adapted to fasten with a respective resinous tissue-piercing part.

* * * * *

UNITED STATES PATENT AND TRADEMARK OFFICE
CERTIFICATE OF CORRECTION

PATENT NO. : 4,767,044
DATED : August 30, 1988
INVENTOR(S) : David T. Green

It is certified that error appears in the above-identified patent and that said Letters Patent is hereby corrected as shown below:

Column 6, line 53, change "FIGS. 23" to --FIG. 23--;

Column 6, line 54, change "appratus" to --apparatus--;

Column 8, line 10, change "...1986. is..." to --1986, which is--;

Column 8, line 63, change "fastener" second occurrence, to -- fasteners --.

Column 10, line 13, change "fastener" to --fasteners--;

Column 10, line 14, change "though" to --through--.

Signed and Sealed this

Thirty-first Day of January, 1989

Attest:

DONALD J. QUIGG

*Attesting Officer*          *Commissioner of Patents and Trademarks*